(12) United States Patent
Wong et al.

(10) Patent No.: US 8,747,335 B2
(45) Date of Patent: Jun. 10, 2014

(54) INTEGRATED SPOT MONITORING DEVICE WITH FLUID SENSOR

(75) Inventors: Daniel Wong, Sunnyvale, CA (US); Christopher D. Wiegel, San Jose, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/459,697

(22) Filed: Apr. 30, 2012

(65) Prior Publication Data

US 2012/0215132 A1 Aug. 23, 2012

Related U.S. Application Data

(60) Continuation of application No. 12/539,849, filed on Aug. 12, 2009, now Pat. No. 8,187,205, which is a continuation of application No. 12/026,190, filed on Feb. 5, 2008, now Pat. No. 7,654,969, which is a division of application No. 11/105,209, filed on Apr. 13, 2005, now Pat. No. 7,351,213.

(60) Provisional application No. 60/562,377, filed on Apr. 15, 2004.

(51) Int. Cl.
*A61B 5/00* (2006.01)
*B65D 81/00* (2006.01)

(52) U.S. Cl.
USPC .............................. 600/584; 600/573; 600/583

(58) Field of Classification Search
USPC ................................................. 600/572–582
See application file for complete search history.

(56) References Cited

U.S. PATENT DOCUMENTS

| | | | |
|---|---|---|---|
| 5,857,983 A | 1/1999 | Douglas et al. |
| 5,879,311 A | 3/1999 | Duchon et al. |
| 5,951,492 A | 9/1999 | Douglas et al. |
| 6,015,392 A | 1/2000 | Douglas et al. |
| 6,048,352 A | 4/2000 | Douglas et al. |
| 6,056,701 A | 5/2000 | Duchon et al. |
| 6,066,085 A | 5/2000 | Heilman et al. |
| 6,099,484 A | 8/2000 | Douglas et al. |
| 6,183,489 B1 | 2/2001 | Douglas et al. |
| 6,315,738 B1 | 11/2001 | Nishikawa et al. |
| 6,319,210 B1 | 11/2001 | Douglas et al. |
| 6,332,871 B1 | 12/2001 | Douglas et al. |
| 6,352,514 B1 | 3/2002 | Douglas et al. |
| 6,612,111 B1 | 9/2003 | Hodges et al. |
| 6,793,633 B2 | 9/2004 | Douglas et al. |
| 6,849,052 B2 | 2/2005 | Uchigaki et al. |

(Continued)

FOREIGN PATENT DOCUMENTS

| | | |
|---|---|---|
| EP | 1 359 418 A1 | 11/2003 |
| EP | 1 426 758 A1 | 6/2004 |
| WO | WO 02/50534 A1 | 6/2002 |
| WO | WO 03/025559 A1 | 3/2003 |

*Primary Examiner* — Rene Towa
(74) *Attorney, Agent, or Firm* — Woodard, Emhardt, Moriarty, McNett & Henry LLP

(57) ABSTRACT

A bodily fluid sampling device is operable to breach the skin surface and allow bodily fluid to emerge from the breach location. The bodily fluid sampling device further evaluates the amount of bodily fluid emerged from breach location and determines whether the amount is sufficient or insufficient for a particular purpose, such as sampling and testing. The determination is accomplished automatically without moving the device. The user may also intervene to perform a variety of tasks following the determination of the amount of bodily fluid.

20 Claims, 7 Drawing Sheets

(56) References Cited

U.S. PATENT DOCUMENTS

| | | |
|---|---|---|
| 7,175,642 B2 | 2/2007 | Briggs et al. |
| 2002/0002344 A1 | 1/2002 | Douglas et al. |
| 2002/0010406 A1 | 1/2002 | Douglas et al. |
| 2002/0077759 A1 | 6/2002 | Cohen et al. |
| 2002/0082522 A1 | 6/2002 | Douglas et al. |
| 2002/0130042 A1 | 9/2002 | Moerman et al. |
| 2003/0083686 A1 | 5/2003 | Freeman et al. |
| 2003/0109808 A1 | 6/2003 | Takinami et al. |
| 2003/0144608 A1 * | 7/2003 | Kojima et al. ............... 600/583 |
| 2003/0208140 A1 | 11/2003 | Pugh |
| 2003/0212344 A1 | 11/2003 | Yuzhakov et al. |
| 2004/0006285 A1 | 1/2004 | Douglas et al. |
| 2004/0073140 A1 | 4/2004 | Douglas et al. |
| 2004/0132167 A1 | 7/2004 | Rule et al. |
| 2004/0162506 A1 | 8/2004 | Duchon et al. |
| 2004/0186394 A1 | 9/2004 | Roe et al. |
| 2004/0242982 A1 | 12/2004 | Sakata et al. |
| 2004/0248312 A1 | 12/2004 | Vreeke et al. |
| 2005/0010134 A1 | 1/2005 | Douglas et al. |
| 2005/0090815 A1 | 4/2005 | Francischelli et al. |
| 2005/0277850 A1 | 12/2005 | Mace et al. |
| 2006/0229532 A1 | 10/2006 | Wong et al. |
| 2009/0024009 A1 | 1/2009 | Freeman et al. |

* cited by examiner

INTEGRATED SPOT MONITORING DEVICE WITH FLUID SENSOR

Reference To Related Applications

The present application is a continuation of U.S. patent application Ser. No. 12/539,849 filed Aug. 12, 2009 now U.S. Pat No.8,187,205, which is a continuation of U.S. patent application Ser. No. 12/026,190 filed Feb. 5, 2008, now U.S. Pat. No. 7,654,969, which is a divisional of U.S. patent application Ser. No. 11/105,209 filed Apr. 13, 2005, now U.S. Pat. No. 7,351,213, which claims the benefit of U.S. Provisional Patent Application No. 60/562,377, filed Apr. 15, 2004, which are hereby incorporated by reference in their entirety.

BACKGROUND

The present invention generally relates to bodily fluid sampling devices and more specifically, but not exclusively, concerns a bodily fluid sampling device configured to evaluate the amount of bodily fluid emerged from a rupture on the surface of skin and determine whether the amount is sufficient or insufficient for testing without the need to move the device.

The acquisition and testing of bodily fluids is useful for many purposes, and continues to grow in importance for use in medical diagnosis and treatment, and in other diverse applications. In the medical field, it is desirable for lay operators to perform tests routinely, quickly and reproducibly outside of a laboratory setting, with rapid results and a readout of the resulting test information. Testing can be performed on various bodily fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like. The fingertip is frequently used as a fluid source because it is highly vascularized and therefore produces a good quantity of blood. However, the fingertip also has a large concentration of nerve endings, and lancing the fingertip can therefore be painful. Alternate sampling sites, such as the palm of the hand, forearm, earlobe and the like, may be useful for sampling, and are less painful. However, they also produce less blood when lanced, thereby increasing the likelihood of that the collected blood sample will be insufficient for accurate test results. For example, if the fluid sample is drawn from the skin onto a test strip prior to the emergence of a sufficient quantity on the skin, the test strip has to be discarded because the test strip is unable to accurately analyze the fluid. Typically, the user then has to lance another site in order to attempt to obtain another sample of fluid. As should be appreciated, this can make monitoring unnecessarily painful as well as expensive.

Sampling devices have been proposed to detect body fluid on the surface of the skin, but these devices still have a number of drawbacks that have prevented the implementation of this fluid detection feature into a successful commercial product. For instance, although these devices are able to alert the user when a sufficient amount of fluid is present on the skin, these sampling devices do not take any actions to automatically increase the amount of fluid when the amount is insufficient. Further, these sampling devices only alert the user when a sufficient amount of fluid is present, and fail to alert the user of fluid insufficiency. By failing to positively alert the user of the fluid insufficiency can make the user question whether the sampling system is working properly. As a result, the user may prematurely remove the sampling device to check its progress before a sufficient amount of fluid can bleed from the incision. Once the device is removed from the skin, automatic fluid collection is practically impossible due to the misalignment created between the incision and the sampling device when the user places the device again over the incision site. Thus, there remains a need for improvement in this field.

SUMMARY

One embodiment concerns a bodily fluid sampling device that includes integrated spot monitoring of emerged bodily fluid. A monitoring, or detecting member, determines the amount of bodily fluid emerged, the rate of emergence of bodily fluid, or both from an opening in the skin's surface. A controller evaluates whether the emerged fluid volume is sufficient for a desired purpose, such as by way of nonlimiting example, testing for particular properties. If the emerged fluid's volume is sufficient, a collection device collects the fluid. If the emerged fluid's volume is insufficient, the collection of the fluid will be delayed until sufficient fluid has emerged.

Another aspect concerns a technique for acquiring a bodily fluid sample with an integrated sampling device. The integrated sampling device includes a skin-contacting member for supporting the device against the skin and a means for rupturing the skin surface. Further, the device includes a means for expressing fluid from the rupture location without removing the skin-contacting member from the skin and a means for collecting the fluid. The means for collecting the fluid includes a collection device with a dosing opening. The skin-contacting member is placed against the skin and, without moving the skin-contacting member from the skin, the skin is lanced to form an incision. Bodily fluid is allowed to move out of the incision site and the amount of fluid is determined without moving the skin-contacting member from the skin. If the fluid amount is determined as insufficient, additional fluid is expressed from the incision without moving the skin-contacting member from the skin. The fluid is then collected from the incision site into the dosing opening.

In a further aspect, the skin in the area of the incision is penetrated to enhance the expression of fluid upon forming the incision. The means by which the additional fluid is expressed may be different from the means by which the fluid is expressed prior to determining its amount.

It is also contemplated that fluid from the incision can be expressed after the skin is lanced and prior to determining the amount of fluid.

It is envisioned that the fluid may be expressed one or more of the following manners: via electrical stimulation, via physical stimulation, mechanically, thermally or via electromagnetic stimulation.

The determination of the amount of fluid may be performed by any one of the following manners: visually, electrically, sonically or electromagnetic detection.

It is also envisioned the determination of whether there is a sufficient amount of fluid at the rupture site can occur after the additional fluid is expressed and before the additional fluid is collected.

It is also contemplated that the device can signal the user after determining that the fluid sample is insufficient. The signaling can also include identifying the need to perform expression of additional fluid.

The skin can be relanced after the device determines that the amount is insufficient and before additional fluid is expressed.

The device can further include a means for testing the fluid for an analyte, which tests the fluid for an analyte after the fluid is collected from the rupture site.

Another aspect concerns a technique for acquiring a bodily fluid sample. An integrated sampling device includes a skin-contacting member for supporting the device against the skin and a means for forming an incision in the skin. The device includes a means for expressing fluid from the incision formed in the skin onto the skin's surface without removing the skin-contacting member from the skin and a means for collecting fluid from the skin's surface. The means for collecting fluid includes a collection device with at least a first dosing opening. The skin-contacting member is placed against the skin, and without moving the member from the skin, the skin is lanced to form an incision, and movement of fluid onto the skin's surface is allowed. Without moving the skin-contacting member from the skin, the device determines that the amount of fluid is insufficient. The sampling device is repositioned, and the steps of placing the skin-contacting member against the skin, lancing the skin without moving the member from the skin, and allowing the movement of fluid onto the skin's surface are repeated. The device can also determine that the amount of fluid is sufficient, and the fluid is then collect from the skin's surface into the dosing opening.

A further aspect concerns a technique for acquiring a fluid sample. An integrated sampling device includes a skin-contacting member for supporting the device against the skin and a means for forming an incision in the skin. The device further includes a means for expressing fluid from the incision formed in the skin without removing the skin-contacting member from the skin and a means for collecting fluid from the incision site that includes a collection device with at least a first dosing opening. The skin-contacting member is placed against the skin and, without moving the member from the skin, the skin is lanced to form an incision, and the movement of fluid out of the incision site is allowed. Without moving the skin-contacting member from the skin, the device determines that the amount of fluid is sufficient, and the fluid is collected from the incision site into the first dosing opening.

Still yet another aspect concerns a technique for acquiring a fluid sample. An integrated sampling device is provided within a housing. The integrated sampling device includes a skin-contacting member for supporting the device against the skin and a means for breaching the skin surface. The device further includes a means for expressing fluid from the breach formed in the skin without removing the member from the skin and a means for collecting fluid from the location that includes a collection device with at least a first dosing opening. The skin-contacting member is placed against the skin and, without moving the member from the skin, the skin is lanced to form an incision. The movement of fluid out of the incision location is allowed. Without moving the member from the skin, the device determines if there is a predetermined amount of fluid at the breach location. Based on the outcome of this determination, one of the following two procedures is performed: (1) prior to collecting fluid, the device determines that the amount of fluid is sufficient and then fluid is collected from the breach location into the dosing opening; or (2) the device determines that the amount of fluid is insufficient and either (a) additional fluid is expressed from the breach location without moving the member from the skin and thereafter collecting fluid, or (b) the sampling device is repositioned and the steps of placing the member against the skin, breaching the skin surface, and determining whether there is a predetermined amount of fluid at the new location, and then performing one of the two procedures are repeated. The additional fluid can be collected through the dosing opening.

Optionally, step (2)(b) of the above-mentioned technique can include determining that the amount of fluid is insufficient.

Also, the determination of whether there is a predetermined amount of fluid on the skin's surface can occur prior to collecting any of the fluid.

At least a portion of the fluid produced by lancing the skin can be collected through the dosing opening prior to determining if there is a predetermined amount of fluid on the skin's surface.

The integrated sampling device can include a second dosing opening, and the additional fluid can be collected through the second dosing opening.

It is contemplated that step (2) of the above-mentioned technique can include expressing additional fluid from the incision, and without removing the member from the skin, again determining if there is a predetermined amount of fluid at the incision location.

Another aspect concerns an integrated sampling device. The integrated sampling device includes a breaching member for breaching the surface of the skin to cause bodily fluid to emerge. The device further includes a sampling device for sampling the emerged bodily fluid and a size determining member for determining the size of the fluid emerged from the ruptured skin prior to the emerged fluid being sampled by the sampling device.

A further aspect concerns an integrated sampling device for bodily fluid that includes a rupturing member for rupturing the surface of the skin to cause bodily fluid to emerge. The device further includes a means for automatically determining whether the emerged bodily fluid is sufficiently sized for sampling and a sampling device for sampling the emerged bodily fluid if the emerged bodily fluid is sufficiently sized. The integrated sampling device can further include a means for automatically expressing additional fluid if the emerged bodily fluid is insufficiently sized.

Still yet another aspect concerns a technique for acquiring a fluid sample that includes providing an integrated sampling device. The skin is lanced to form an incision, and movement of fluid onto the skin surface is allowed. The amount of fluid on the skin surface is determined, and, based on the determination of the amount of fluid, proceeding with either: (1) determining that the amount of fluid is insufficient and either (a) expressing additional fluid and repeating the determination, or (b) repeating the determination; or (2) determining that the amount of fluid is sufficient and collecting the fluid. The integrated sampling device can include a means for forming an incision in the skin, a means for expressing fluid from the incision onto the skin surface, and a means for collecting fluid from the incision location.

Another aspect concerns a body fluid sampling device that includes a lancing device configured to create an incision in a surface of tissue. A fluid detector is configured to detect sufficiency of body fluid bled from the incision while on the surface of the tissue, and an expression device is operatively coupled to the fluid detector. The fluid detector is configured to have the expression device automatically express the body fluid from the incision upon detecting that the body fluid on the surface of the tissue is insufficient for analysis. An analysis device is configured to analyze the body fluid once the fluid detector detects that the body fluid on the surface of the tissue is sufficient for analysis.

A further aspect relates to a body fluid sampling device that includes a test strip. The test strip includes a capillary channel for drawing body fluid from a tissue and an analysis portion located along the capillary channel for analyzing the body fluid. The test strip has a fluid detector to sense sufficiency of the body fluid on the tissue before the body fluid is drawn into the capillary channel.

Another aspect concerns a method in which a sampling device is placed against tissue. An incision is created in the tissue with the sampling device, and the sampling device detects that body fluid bled from the incision on the tissue is insufficient for analysis, and in response, the body fluid is expressed from the incision automatically with the sampling device while the sampling device remains against the tissue.

Further forms, objects, features, aspects, benefits, advantages, and embodiments of the present invention will become apparent from a detailed description and drawings provided herewith.

DESCRIPTION OF SELECTED EMBODIMENTS

Figure 2:
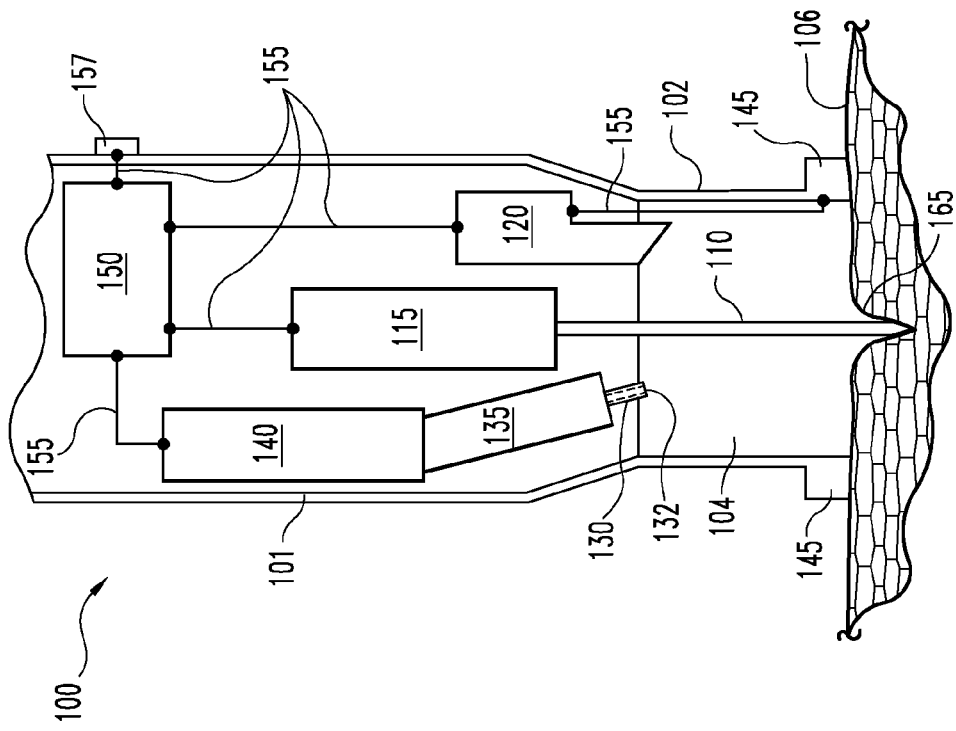
FIG. 2 is a cross-sectional view of the FIG. 1 device during lancing.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

In one embodiment, a bodily fluid sampling device is operable to detect the amount of emerged bodily fluid available for sampling from an incision in the surface of skin or other tissue. In another embodiment, the bodily fluid sampling device is operable to detect the rate of emergence of bodily fluid from the incision. While still in other embodiments, the bodily fluid sampling device detects both the amount and the rate of emergence of bodily fluid from the incision. The bodily fluid sampling devices further determine whether the amount of fluid is sufficient, or insufficient, for sampling. After the amount, or rate of emergence, of bodily fluid is determined, the device can automatically intervene to perform a variety of tasks, such as expressing the fluid, or in addition, the user can intervene, if so desired. For instance, when an insufficient amount of fluid is present on the skin, the device can continue to automatically express additional fluid, either actively or passively, or sample the fluid regardless of whether it is insufficient.

Figure 1:
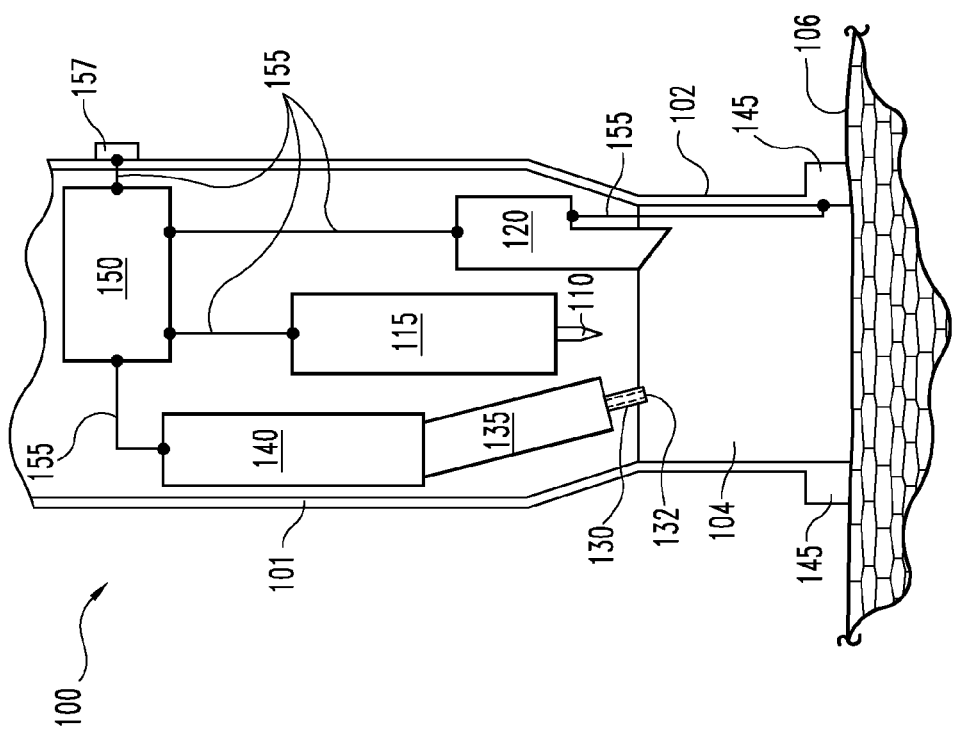
FIG. 1 is a cross-sectional view of a bodily fluid sampling device according to one embodiment.

A bodily fluid sampling device 100 according to one embodiment, among many, is illustrated in FIGS. 1, 2, 3 and 4. The sampling device 100 includes a housing 101 with a skin-contacting or standoff member 102, and the housing 101 defines an internal cavity or collection chamber 104. As shown in FIG. 1, the skin-contacting member 102 is configured to be placed against skin or tissue 106. It should be recognized that the sampling device 100 can collect fluid from other types of tissues, in addition to skin, and can collect fluid from human as well as animal subjects. In the collection chamber 104, the sampling device 100 includes an incision forming device 110 for rupturing the skin 106. The incision forming device 110 in the illustrated embodiment includes a lancet, but it should be appreciated that other types of devices for rupturing the skin 106 can be used. For instance, the incision forming device 110 in other embodiments can include a blade, a laser, a pneumatic type lancet and/or a hydraulic type lancet, to name a few. The lancet 110 can be made of various materials capable of rupturing the skin surface 106, for example, surgical stainless steel, plastics, fiber composites, and/or ceramics. In the illustrated embodiment, a firing mechanism or lancet actuator 115 is coupled to the lancet 110 for firing the lancet 110 to form an incision in the skin 106. The actuator 115 in one embodiment includes an electric motor, and in another embodiment, the actuator 115 includes one or more springs for firing and retracting the lancet 110. However, it should be appreciated that the actuator 115 can include other types of firing devices, such as a pneumatic or hydraulic motor.

Referring to FIG. 1, the integrated sampling device 100 further includes a detector 120 for determining the amount of body fluid that emerges from an incision. In alternate embodiments, the detector 120 determines the rate of emergence of bodily fluid. It is contemplated that the detector 120 in other embodiments can be configured to detect other properties as well. In one embodiment, the detector 120 detects the fluid sample ultrasonically. When detecting fluid ultrasonically, the detector 120 includes a transducer that generates an ultrasonic field within the collection chamber 104 and a receiver that receives reflected ultrasound waves. The detector 120 detects the fluid sample based on the change in the resonance of the ultrasonic field in the collection chamber 104 as fluid fills the cavity 104. As should be appreciated, the detector 120 in other embodiments can detect fluid in other manners. It is contemplated that the body fluid in other embodiments can be detected via a vision system, electrically, and/or through thermal imaging, for example. For instance, the detector 120 in another embodiment includes a position sensing detector (PSD), which can be a one or two axis type PSD that triangulates the location of the drop of body fluid. In another example embodiment, the detector 120 includes a charge couple device (CCD) that triangulates the location of the body fluid drop and/or measures the size and/or shape of the drop.

Although the detector 120 is depicted as a single unit, in other embodiments the detector 120 includes multiple elements, such as an array of sensors.

Also included in the sampling device 100 is a collection device 130 with a dosing opening 132 for collecting a sample of the body fluid. In the illustrated embodiment, the collection device 130 includes a capillary tube, but it is envisioned that other types of collection devices can be used. The collection device 130 can include a test strip and/or wicking material, for example. A collection device actuator 135 is used to place the collection device 130 in fluid communication with the bodily fluid, although other embodiments do need the collection device actuator 135, such as when the collection device 130 is fixed so that the dosing opening 132 is already positioned over the incision site. Due to variations in the properties of skin, such as elasticity, the distance that the collection device 130 must travel to collect a fluid sample can vary. In one embodiment, the detector 120 acts as a range finder to ultrasonically determine the location of the surface of the skin 106 and/or the body fluid. Based on the determined location, the collection actuator device 135 can adjust how far the collection device 130 extends toward the skin.

A testing device 140 for testing the bodily fluid sample for particular properties is fluidly coupled to the collection device 130 via the collection device actuator 135 to receive the body fluid from the collection device 130. In one embodiment, the testing device 140 is in the form of an electrochemical sensor that tests the fluid based on the electrochemical properties of the fluid.

As should be appreciated that testing device 140 can test the body fluid sample in other manners. For example, the testing device 140 can test the fluid sample in other manners, such as chemically and/or optically, to name a few. As shown in FIG. 1, the sampling device 100 includes an expression device 145 that is positioned proximal to the skin 106 for expressing body fluid from an incision. Expression device 145 can use a variety of techniques to express additional bodily fluid, such as by way of nonlimiting example, thermal heating, electrical stimulation, vacuum, additional lancing, vibration, and/or kneading. In one embodiment, the expression device 145 is used to mechanically express fluid from an incision, and in particular, the expression device 145 includes a ring shaped member that is pressed against the skin 106 to express fluid. It is envisioned that the expression device can express fluid in other manners. For example, in another embodiment, the expression device 145 expresses fluid by electrically stimulating the skin with an array of electrodes. In other forms, the expression device 145 can express body fluid thermally, via a vacuum and/or by spraying an anticoagulant at the incision site, for instance. Although the lancet 110, the collection device 130, the testing device 140 and the detector 120 in the illustrated embodiment are shown as separate components, it should be appreciated that two or more of these components can be integrated into a single unit. As an example, the lancet 110, the collection device 130 and the testing device 140 can be incorporated into an integrated lancing test strip of the type disclosed in U.S. patent application Ser. No. 10/330,724, filed Dec. 27, 2002, which is hereby incorporated by reference in its entirety. Likewise, it is envisioned that other components of the sampling device 100 can be integrated together.

The sampling device 100 further includes a controller 150 to coordinate the operation of the lancet actuator 115, the detector 120, the collection device actuator 135, the testing device 140, and the expression device 145. As depicted, the controller 150 is operatively coupled directly to three components, the lancet actuator 115, the detector 120 and the testing member 140, and indirectly coupled to two other components, the expression device 145 and the collection device actuator 135, by communication pathways 155. It nevertheless should be appreciated that the components in the sampling device 100 can be coupled to the controller 150 in other manners, such as via a wireless connection, and/or in a different configuration. For example, the expression device 145 in other embodiments can be operatively coupled to the controller 150 in a direct manner. As should be appreciated the controller 150 can communicate with the components of the sampling device 100 via a number of manners, such as through a serial or parallel interface. As shown in FIG. 1, an input/output (I/O) device 157 is mounted on the housing 101 and is operatively coupled to the controller 150. Via the I/O device 157, the controller 150 is able to display messages to the user and receive commands from the user. For example, the user can actuate the I/O device 157 to fire the lancet 110, and once the body fluid sample from the incision is analyzed, the I/O device 157 can display the results to the user. It nevertheless should be appreciated that the I/O device 157 can perform other types of functions. In one embodiment, the I/O device 157 includes a display and one or more entry buttons. Although the I/O device 157 is illustrated as an integrated unit, it should be appreciated that the input and output components of the I/O device 157 can be configured as separate components. It is contemplated that sampling device 100 in other embodiments may have only an input device or an output device. The I/O device 157 can include any type of input and/or output device as would occur to those skilled in the art. For instance, the I/O device 157 can incorporate keypads, microphones, speakers, displays, lights as well as other types of input and/or output devices.

A technique, according to one embodiment, for collecting body fluid 160 from an incision 165 will now be described with reference to flowchart 200 in FIG. 5. In stage 202, the sampling device 100 is placed in contact with the skin 106, as is depicted in FIG. 1. Once placed against the skin 106, the expression device 145 in one embodiment is used to prime the incision site before the incision is formed by drawing body fluid 160 within the skin 106 towards the incision site. For example, the expression device 145 can be pressed against the skin 106 in order to prime the incision site. In another form, the expression device 145 electrically stimulates the skin 106 to draw body fluid to the incision site, and in still yet another form, the expression device 145 heats the skin 106 to prime the incision site. It should be appreciated that the incision site can be primed in other manners, however. For example, a vacuum can be used to prime the site. Further, it is envisioned that in other embodiments a separate device can be used to prime the incision site before the sampling device 100 is placed against the skin 106 in stage 202. In still yet another embodiment, the incision site is not primed before an incision is formed.

Referring to FIG. 2, while remaining in contact with the skin 106, the sampling device 100 in stage 204 fires the lancet 110 to form the incision 165 in the skin 106. The lancet 110 can be fired automatically by the sampling device 100 or manually by the user. To fire manually, the user actuates the I/O device 157, which sends a firing signal to the controller 150. To automatically fire, the detector 120 in one embodiment detects the presence of the skin 106, and upon detecting the skin 106 (or after a predetermined delay), the detector 120 sends a firing signal to the controller 150. In one form where an ultrasonic type detector is used, the detector 120 sends the firing signal to the controller 150 when the detector 120 senses an ultrasonic resonance that indicates placement of the device 100 against the skin 106. In other embodiments, the lancet actuator 115 is activated by mechanisms other than the controller 150, such as through a mechanical linkage when sufficient pressure is generated between the skin-contacting member 102 and the skin 106. After receiving the appropriate signal from the controller 150, the lancet actuator 115 moves the lancet 110 to rupture the skin 106, and once the incision 165 is formed, the lancet 110 is retracted. It should be understood that the lancet 110 can be fired in other manners. As mentioned before, the incision can be formed in stage 204 with other types of devices besides that lancet 110, such as with a laser. During formation of the incision 165, the expression device 145 can continue to prime the incision site so that the body fluid rapidly discharges from the incision 165, once formed. Alternatively, the priming can cease before the incision 165 is formed.

Figure 3:
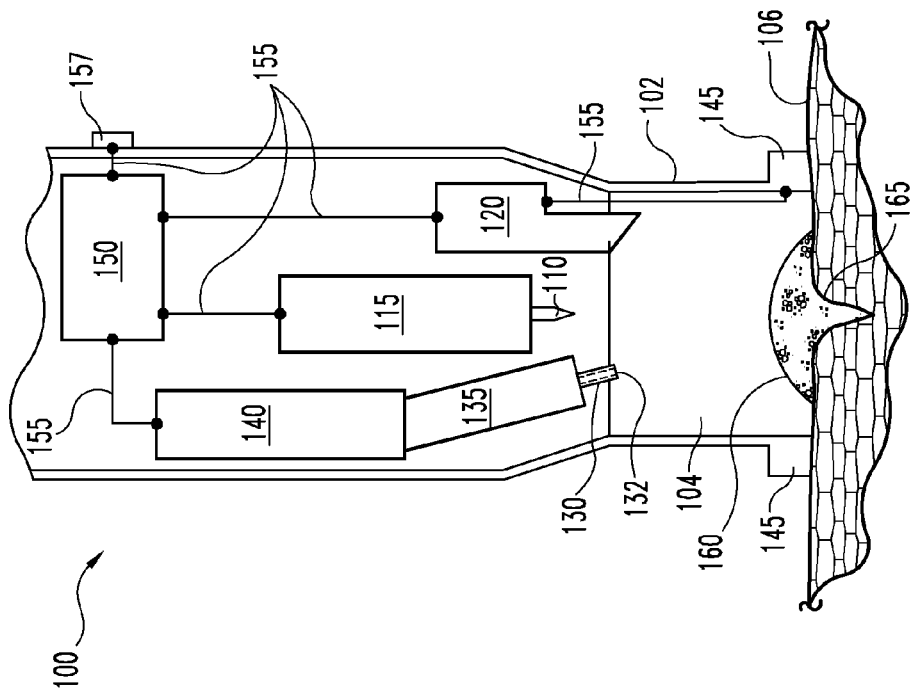
FIG. 3 is a cross-sectional view of the FIG. 1 device with emerged fluid at the lancing site.

After rupturing the skin 106, body fluid 160 tends to naturally emerge from the incision 165, as is illustrated in FIG. 3. If needed, discharge of the body fluid 160 from the incision 165 can be enhanced with the expression device 145. For example, the expression device 145 in one embodiment is pressed against the skin 106 to force additional body fluid 160 from the incision 165. In another embodiment, the body fluid 160 is allowed to naturally bleed from the incision 165 without the assistance of the expression device 145. Without removing the device 100 from the skin 106, the detector 120 in stage 206 determines whether an adequate amount of body fluid 160 has emerged from the incision 165. The adequacy or sufficiency of the amount of body fluid 160 is based on the amount of body fluid 160 required to sample and analyze with the testing device 140 to assure generally accurate results. It should be understood the fluid sufficiency amount can as well incorporate other factors, such as a safety margin. For instance, if a 1 μL or greater sample size is required for accurate results, then a 0.5 μL safety margin can be added to account for fluid loss during sampling, thereby resulting in a 1.5 μL fluid sufficiency amount. As testing technology improves, the amount of fluid required can in turn be less than 1 μL. In certain embodiments, the detector 120 determines whether the amount of emerged body fluid 160 exceeds a minimum threshold. While in other embodiments, the detector 120 periodically (or continuously) measures the amount of emerged body fluid 160 and relays this information to the controller 150, which makes a determination whether the emerged body fluid 160 is accumulating at a sufficient rate or exceeds a predetermined threshold. In still other embodiments, the detector 120 directly measures the rate at which the emerged body fluid 160 is accumulating. It is contemplated that the detector 120 in other embodiment can detect the sufficiency of the fluid sample in a binary fashion, that is, whether or not a sufficient fluid level has been reached. While the detector 120 is detecting the sufficiency of the fluid sample, the I/O device 157 in one embodiment can notify the user of whether or not a sufficient sample of body fluid 160 has collected on the skin 106. For example, in one embodiment, the I/O device 157 includes an indicator light emitting diode (LED) that illuminates only when a sufficient amount of fluid 160 is collected, and in another embodiment, the LED darkens when a sufficient amount of fluid is collected. In still yet further forms, the LED displays a "wait", "fluid insufficient" or other types of messages to positively indicate that the body fluid 160 bled thus far is insufficient for testing, and the LED can display a "testing", "fluid sufficient" or other similar messages to affirmatively indicate that the detected body fluid 160 is enough for testing purposes. Positively indicating fluid insufficiency reduces the chance that the user will prematurely remove the device 100 from the skin 106, which would make automatic fluid sampling practically impossible. It should be understood that the I/O device 157 can indicate body fluid sufficiency in other manners, or not at all.

As noted before, various techniques may be utilized to determine whether the emerged bodily fluid 160 is increasing in size, increasing in size at a particular rate, or exceeds a particular volume or mass. By way of non-limiting examples, the detector 120 can detect the volume or mass of the emerged bodily fluid 160 either directly, indirectly, actively or passively through the use of sonar, electromagnetic radiation, photometric evaluation, thermal detection, electro-optical evaluation, and/or electrochemical evaluation. The sensing techniques can determine the amount a particular sensing medium is absorbed, dispersed, scattered, attenuated, refracted, reflected, fluoresced or diffused. Additionally, the known rate of change of a particular property of the emerged bodily fluid 160, such as temperature by way of nonlimiting example, may be detected to determine volume or mass. In certain embodiments, the detector 120 utilizes the size of the collection chamber 104 in making the volume or mass determination.

As previously mentioned, the detector 120 in one embodiment includes an ultrasonic detector that detects the amount of fluid based on the ultrasonic resonance of the collection chamber 104 when placed against the skin 106. The detector 120 in this embodiment includes a transducer that generates an ultrasonic field in the collection chamber 104 and a receiver that monitors the ultrasonic field. Once the skin 106 is lanced, the detector 120 monitors the ultrasonic field for changes. As body fluid 160 emerges from the incision 165, the volume of air inside the collection chamber 104 is reduced, which changes the resonance of the ultrasonic field inside the chamber 104 (in a manner analogous to a wind instrument). The controller 150 and/or the detector 120 maintains records of the correlation between changes in the resonance of the ultrasonic field and the reduction of the air volume in the collection chamber 104. As should be appreciated, the reduction of air volume in the collection chamber 104 is inversely proportional to the volume of body fluid 160 inside the collection chamber 104. That is, as more body fluid 160 fills the chamber 104, less air occupies the collection chamber 104, which in turn changes the resonance of the collection chamber 104. Based on the change of the resonance of the chamber 104, the detector 120 is able to detect the adequacy of the body fluid sample. Although the detector 120 is described as making the determination as to the sufficiency of the sample, it should be understood that the controller 150 in other embodiments make this determination based on readings received from the detector 120.

Figure 4:
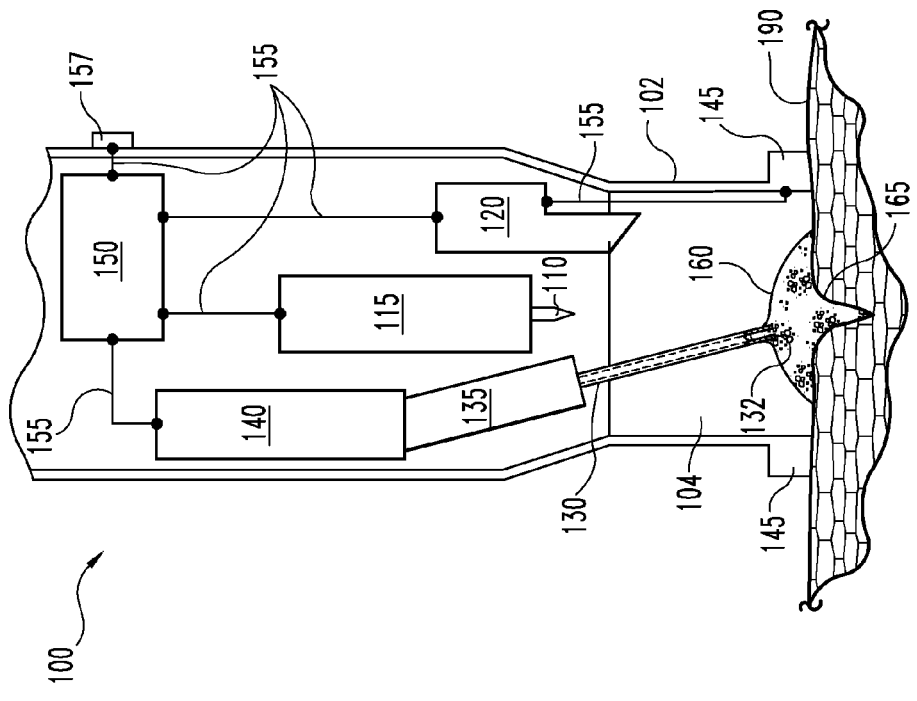
FIG. 4 is a cross-sectional view of the FIG. 1 device during sampling.

When in stage 208 the detector 120 determines that a sufficient amount of body fluid 160 has collected on the skin 106, the controller 150 causes the collection member actuator 135 in stage 208 to extend the collection device 130 so that the body fluid 160 is collected via the dosing opening 132, as is illustrated in FIG. 4. As noted above, the collection device 130 can collect the body fluid 160 in a number of manners, such as by drawing the body fluid 160 via capillary action, a vacuum or a combination of both, for example. After the body fluid sample is collected, the testing device 140 analyzes the sample, and the controller 150 provides the results of the analysis to the user via the I/O device 157.

Figure 5:
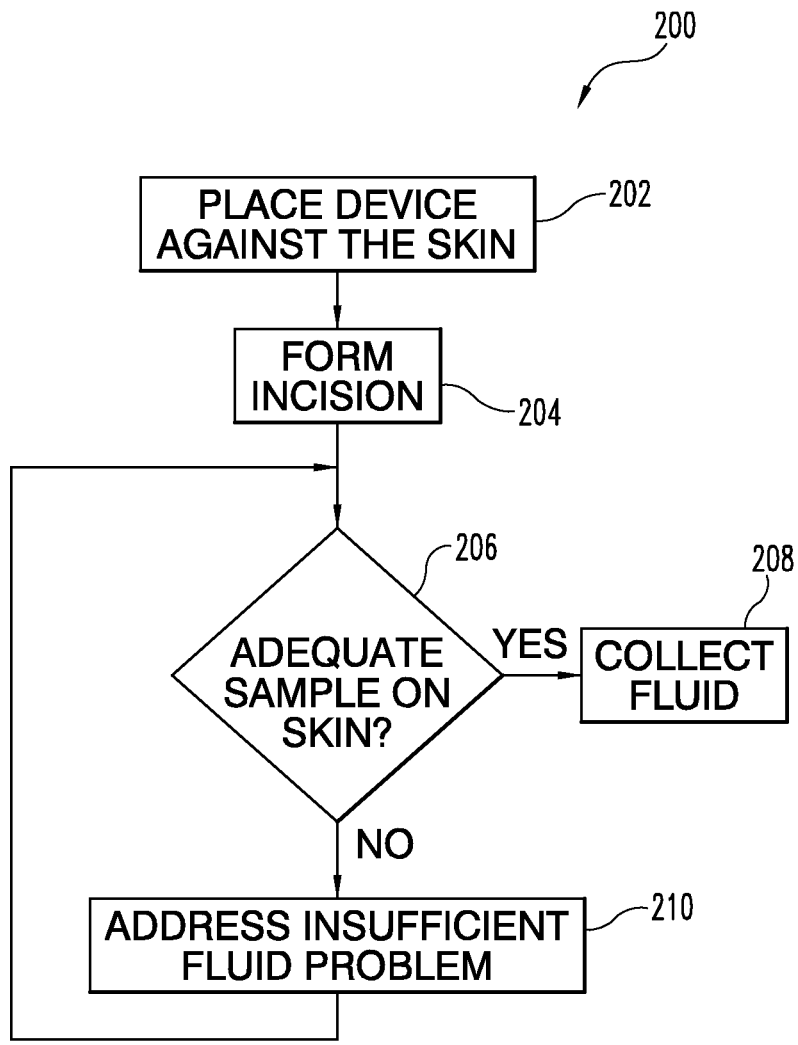
FIG. 5 shows a flow diagram that illustrates a technique for collecting fluid according to one embodiment.

On the other hand, when the detector 120 detects that the sample of body fluid 160 on the skin 106, the inadequate fluid sample problem is addressed in stage 210, as is depicted in FIG. 5. The sampling device 100 in one embodiment considers the sample to be inadequate when a threshold fluid amount is not reached within a specified period of time. In another embodiment, the fluid sample is considered insufficient when the amount of fluid has not increased at a significant rate within a certain time interval. A combination of these two techniques can also be used to detect sufficiency in other embodiments. It is further envisioned that other parameter can be used to determine that the amount of fluid was inadequate for testing purposes. For example, the sampling device 100 in another embodiment does not set time limits for determining sample adequacy. Rather, the sampling device 100 continuously addresses the insufficiency of the body fluid 160 in stage 210, such as by expressing fluid, until an adequate amount of body fluid 160 is detected on the skin 106 in stage 206.

In stage 210, the insufficiency of the body fluid sample can be addressed automatically by the sampling device 100, or by a combination of both automatic and manual techniques. In one embodiment, the expression device 145 is used to express additional fluid 160 from the incision 165 in stage 210. Expression device 145, as noted before, can use a variety of techniques to express additional body fluid 160 from the incision 165, such as by way of nonlimiting example, thermal heating, vacuum, mechanically pressing the skin 106, electrical stimulation, vibration, and/or kneading. For example in one embodiment, after an inadequate amount of body fluid 160 is detected, the controller 150 activates in stage 210 the expression device 145 to electrically stimulate the skin 106 so as to express additional fluid 160 from the incision 165. While the expression device 145 expresses the body fluid 160, the detector 120 monitors the amount of body fluid 160 on the skin 106. Once an adequate amount of fluid 160 is detected, the controller 150 deactivates the expression device 145, and the body fluid 160 is collected in stage 208. In another embodiment, the controller 150 deactivates the expression device 145 before detecting the amount of body fluid 160 on the skin with the detector 120. For instance, when the body fluid 160 is expressed through mechanical pressure, readings from the detector 120 may become distorted by misshapening of the skin 106. This especially can occur when detecting fluid 160 ultrasonically.

After each failure in stage 206, the sampling device 100 can continue to use the same technique to draw additional fluid 160 from the incision 165 or can vary the technique used. For example, after failing to draw a sufficient amount of fluid 160, the controller 150 via the I/O device 157 in one embodiment instructs the user to manually press the device 100 against the skin 106 in an attempt to express additional fluid 160. In stage 210, the lancet 110 can be also used to draw additional fluid 160 onto the skin 106. In one embodiment, after forming the incision in stage 204, the lancet 110 remains in the incision 165 to brace the incision 165 open, thereby allowing additional body fluid 160 to flow from the incision 165. While in the incision 165, the lancet 110 can for example be moved, rotated, reciprocated, and/or vibrated to draw additional fluid 160. In another embodiment, the lancet 110 re-lances the skin 106 in order to improve the amount of body fluid 160 on the skin 106. In one form, the lancet 110 lances at the same incision 165 again, but at a greater depth in order to improve the chances of cutting a sufficient number of capillaries in the skin 106. In another form, the controller 150 repositions the lancet 110 within the device 100, or uses a second lancet 110 that is offset from the first lancet 110, and fires the lancet 110, so that a second incision is formed that is offset from the original incision 165. The lancet 110 in still yet a further form is reoriented to an oblique angle relative to the skin 106 so that an obliquely angled incision 165 is formed in the skin 106, which increases the chance of cutting more capillaries. In stage 210, the sampling device 100 can use a delay feature in which no action is taken so as to allow the body fluid 160 to naturally emerge from the incision 165 for a period of time.

As previously mentioned, the user can intervene in stage 210 so as to manually address the insufficient fluid problem. For example in one embodiment, once the controller 150 determines that an insufficient amount of body fluid 160 is present, the controller 150 alerts the user to the problem with the I/O device 157. As should be appreciated, the user in stage 210 can address the fluid insufficiency problem in many ways. Upon being alerted, the user can press the sampling device 100 against the skin 106 so as to express additional fluid 160 from the incision 165, for example. In another manner, the user can remove the sampling device 100 from the skin 106 so as to minimize constriction of fluid flow within the skin 106 towards the incision 165. After predetermined amount of time, the sampling device 100 can instruct the user to again place the sampling device 100 over the incision 165 so that the body fluid 160 can be collected (stage 208). In still yet another embodiment, upon determining that the amount of fluid 160 is insufficient, the sampling device 100 instructs the user to reposition the sampling device 100 over a different part of the skin 106, away from the incision 165. Once repositioned, the sampling device 100 forms a second incision (stage 204), detects the adequacy of the fluid sample (stage 206), and if needed, addresses any insufficient fluid problems (stage 210) before collecting the fluid 160 (stage 208). The sampling device 100 in a further form is configured to permit a manual override by the user. Even if the sampling device 100 detects an insufficient amount of fluid, the user through the I/O device 157 can still command the sampling device 100 to collect the body fluid 160.

It is envisioned that a combination of manual and automatic techniques can be used to address the insufficient fluid problem. In one embodiment, the sampling device 100 first attempts to automatically address the insufficient fluid problem in stage 210 before requesting user intervention. For instance, the sampling 100 can initially express fluid by electrically stimulating the skin 106 with the expression device 145, and after a predetermined number of attempts and/or a specified time period, the sampling device 100 alerts the user to the problem with the I/O device 157 so that the user can manually address the problem in stage 210. In another embodiment, the sampling device 100 is configured to allow the user to first manually address the problem before the sampling device 100 automatically addresses the problem in stage 210. Further, it is contemplated that the sampling device 100 can utilize a combination of the above-described techniques at the same time in stage 210. For instance, the user can manually press the device 100 against the skin 106, while at the same time, the expression member 145 electrically stimulates the skin 106.

With the detector 120, the sampling device 100 is able to detect the sufficiency of the fluid sample before the body fluid 160 is even drawn into the collection device 130, which reduces waste. For example, test strips are not wasted, when the collection device 130 uses a test strip to collect the fluid. Also, when in an automatic operation mode, the sampling device 100 is able to obtain a sufficient amount of fluid without the need of removing the device 100 from the skin 106. If for instance the device 100 was removed from the skin 106, or even slightly moved, the automatic collection of the body fluid 160 in a consistent manner can be difficult. Upon removal of the sampling device 100, the collection device 130 can become misaligned with respect to the body fluid 160 from the incision 165 so that the dosing opening 132 is unable to contact the fluid 160 when extended.

It is envisioned that the sampling device 100 is robust enough to handle the situation in which the user accidentally removes the sampling device 100 from the skin 106. For example, if the sampling device 100 is accidentally removed after the skin 106 is lanced, the user can reposition the sampling device 100 over the incision site so that the sampling device can detect the sufficiency of the fluid, express any additional fluid (if needed), sample the fluid and analyze the fluid. In still yet another example, where the sampling device 100 is accidentally removed from the skin 106 after an insufficient amount of fluid is detected, the user can manually express the fluid from the skin 106 such as by squeezing the skin 106. Afterwards, the user can manually collect the fluid with a test strip, for example, or the sampling device 100 can be repositioned over the incision site so as to automatically collect and analyze the fluid.

Figure 6:
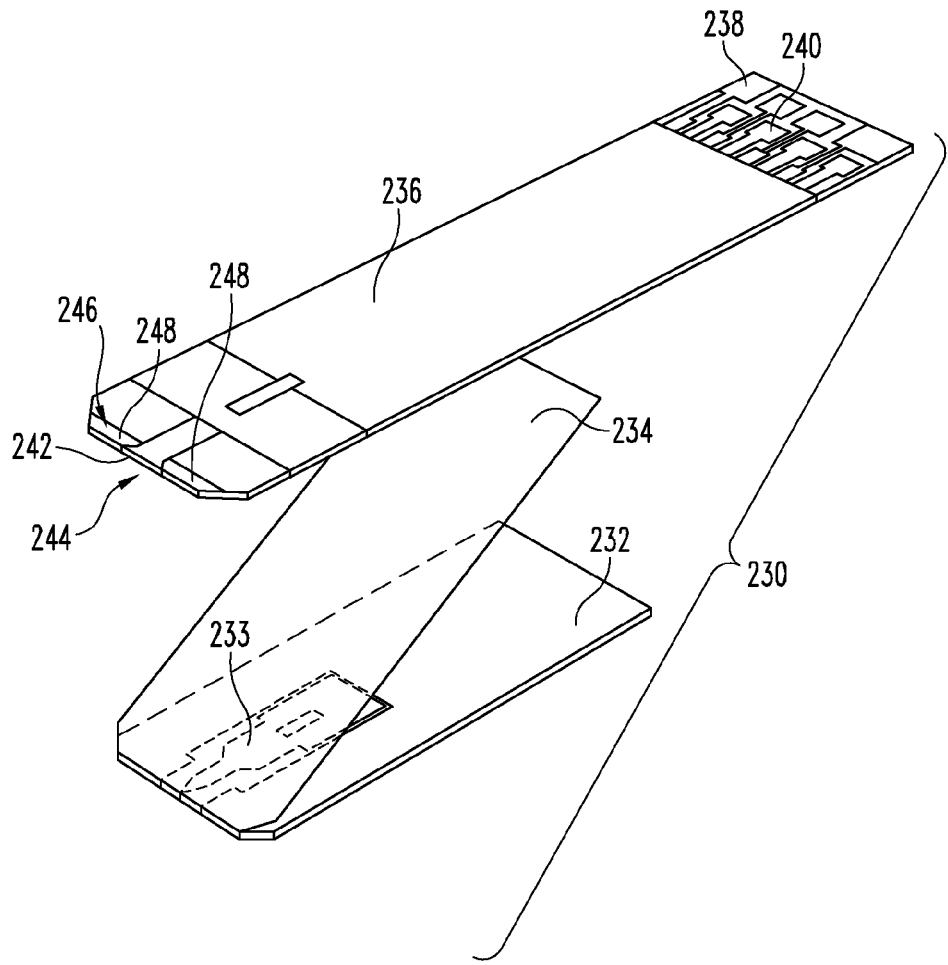
FIG. 6 is an exploded view of an integrated lancing test strip according to one embodiment.
Figure 7:
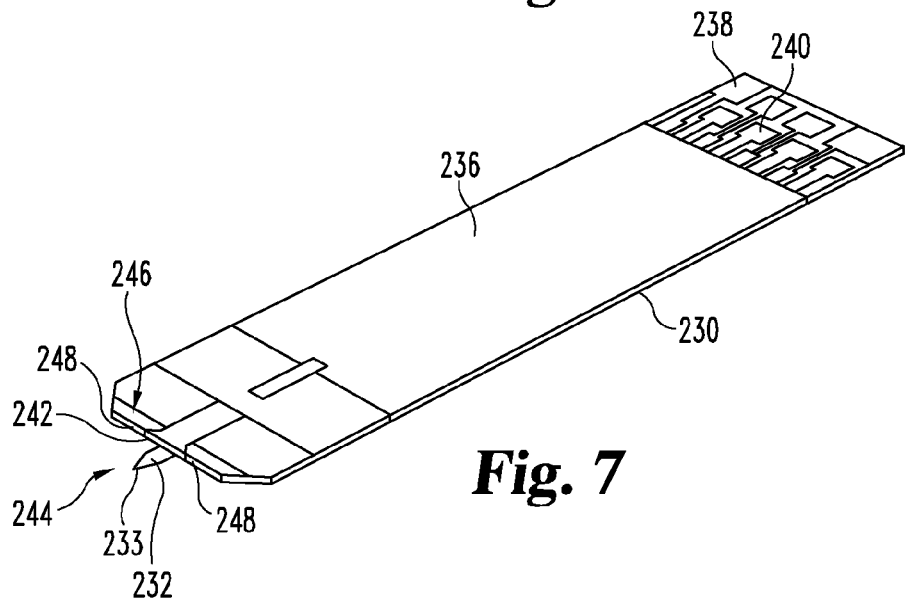
FIG. 7 is a top perspective view of the FIG. 6 integrated lancing test strip with its lancet in an extended position.
Figure 8:
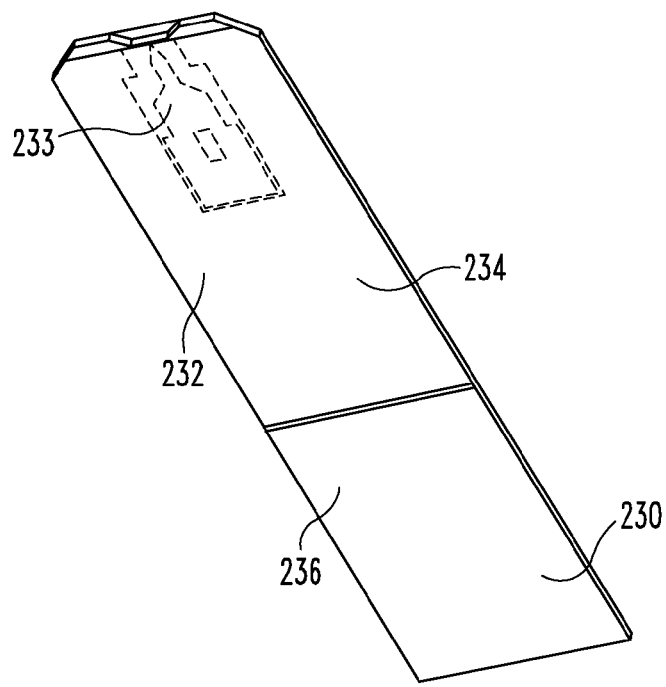
FIG. 8 is a bottom perspective view of the FIG. 6 integrated lancing test strip with the lancet in a retracted position.

As mentioned previously, an integrated lancing test strip can be used to sample and analyze fluid using the above-described techniques. An integrated lancing test strip 230, according to one embodiment, that can be used in conjunction with the above-described techniques is illustrated in FIGS. 6, 7 and 8. It should be recognized that the previously described sampling device 100 can be modified to sample fluid with the illustrated integrated lancing test strip 230. The integrated lancing test strip 230 in the illustrated embodiment shares a number of components in common with those described in U.S. patent application Ser. No. 11/070,502, filed Mar. 2, 2005, which is incorporated by reference in its entirety, and for the sake of clarity as well as brevity, these common components will not be described in great detail below.

In one embodiment, the integrated lancing test strip 230 in one form incorporates a fluid detector that senses whether the body fluid bled from an incision is sufficient enough for testing purposes. During sampling, body fluid can tend to smear or splatter, which in turn can contaminate the fluid detector or other components inside the sampling device. Once contaminated, the fluid detector has to be cleaned and sterilized. By having the fluid detector incorporated into the integrated lancing test strip 230, the need to clean the detector after every use is eliminated because the contaminated detector is disposed of after every test. There is a trend that as test strip technology improves the required sample sizes for testing become smaller. With the fluid detector incorporated on the integrated lancing test strip 230, the fluid detector can be configured to detect fluid sample sizes that are specifically needed for the integrated lancing test strip 230. Thus, as test strip technology improves, the user does not have to necessarily purchase a new sampling device or meter in order to gain the benefits of smaller sample sizes. Further, with the detector positioned on the integrated lancing test strip 230, smaller sample sizes can be detected without having the detector interfere with fluid collection. The integrated lancing test strip 230 can be placed into close proximity to the sample such that smaller sample sizes can be readily detected. Further, the detector allows the integrated lancing test strip sense its position so as to enhance fluid collection by allowing accurate positioning of the integrated lancing test strip 230. Although the test strip in the illustrated embodiment incorporates a lancet, it should be recognized that the fluid detector can be incorporated into other types of test strips that do not have lancets.

As depicted in FIGS. 6 and 7, the integrated lancing test strip 230 includes a lancet assembly or incision forming member 232 with a moveable lancet needle 233 for forming an incision in tissue, a sterility sheet or foil 234 for maintaining the sterility of the lancet 232, and a test strip 236 for acquiring a body fluid from the incision. The lancet needle 233 has an opening where the firing mechanism engages the needle 233 when lancing the skin. During lancing the lancet needle 233 slides within the lancet assembly 232 and punctures the sterility sheet 234. After forming the incision, the needle 233 is retracted back inside the sterility sheet 234. Both the lancet 232 and the test strip 236 in the illustrated embodiment are generally flat such that the integrated lancing test strip 230 has an overall flat appearance. By being flat, multiple integrated lancing test strips 230 can be incorporated into magazines, cassettes, drums, cartridges and the like, which allows a plurality of integrated lancing test strips 230 to be used without the need to individually load and/or dispose of used integrated devices 230. For example, the overall flat shape allows multiple integrated lancing test strips 230 to be stacked upon one another in a magazine or rolled around a reel in a cassette. Furthermore, the overall flat shape allows the integrated lancing test strip 230 to be manufactured with a continuous process in which layers of component materials can be layered to form contiguous strips of integrated lancing test strips 230 that can be cut to form individual units or remain attached for use in cassettes and the like. It should nonetheless be recognized that the integrated lancing test strip 230 in other embodiments can have a different overall shape.

In the illustrated embodiment, the test strip 236 is an electro-chemical type test strip. In one particular form, the test strip 236 includes a modified version of an ACCU-CHEK® brand test strip (Roche Diagnostics GmbH), but it is envisioned that other types of test strips can be used. For example, the test strip 236 in other embodiments can include an optical type test strip or can analyze fluid samples in other manners. At one end, the test strip 236 in the illustrated embodiment includes a connection portion 238 with electrical contacts 240 that transmit sample readings to a meter, as is shown in FIGS. 6 and 7. Opposite the connection portion 238, the test strip 236 has a capillary channel 242 with a capillary opening 244 that is configured to draw a body fluid sample from an incision formed by the lancet 232 via capillary action. As should be appreciated, the test strip 236 inside the capillary channel 242 includes an analysis region with electrodes, like working, counter and reference electrodes, and reagents for analyzing the fluid sample. In one form, the connection portion 238 is connected to a meter, and the sample readings from the electrodes in the analysis region are transmitted to the meter via the electrical contacts 240.

With continued reference to FIGS. 6 and 7, at the end opposite the connection portion 238, the test strip 236 has a fluid detector 246 for sensing the amount or rate of emergence of body fluid from an incision. The detector 246 can also be used for range finding purposes to locate the position of the test strip 236 relative to the skin and/or the drop of body fluid. It should be appreciated that in other embodiments features from the integrated lancing test strip 230 can be incorporated into systems in which all or part of the detector 246 is separate from the test strip 236. In the illustrated embodiment, the detector 246 includes a pair of sensors 248 that are positioned on opposite sides of the capillary opening 244. However, it is contemplated that the detector 246 in other embodiment can include one or more sensors 248. Further, the sensors 248 in other embodiments can be positioned at other locations on the integrated lancing test strip 230. For example, it is contemplated that all or part of the detector 246 can be located on the lancet 232, or the detector 246 can be positioned away from the capillary opening 244. The sensors 248 are operatively coupled to the electrical contacts 240 so that the readings from the detector 246 can be transferred to the sampling device or meter. In one embodiment, the sensors 248 act like capacitor plates that measure the capacitance between the detector 246 and the surface of the skin or tissue. As body fluid bleeds from an incision, the space between the surface of the skin and the sensors 248 fills with body fluid, which in turn changes the capacitance between the detector 246 and the skin. With the capacitance measurements, the sampling device is able to determine the flow rate and/or amount of body fluid from the incision. Furthermore, the sampling device can use the capacitance measurements for range finding so as to determine the distance between the end of the test strip 236 and the skin. This can be used to ensure that the capillary opening 244 is positioned properly to collect fluid. For instance, if the test strip 236 is pressed too hard against the skin, fluid flow from the incision could become constricted. On the other hand, if the test strip 236 is positioned too far away, the capillary channel 242 in the test strip 236 will not be able to collect the fluid. Alternatively or additionally, the capacitance between the sensors 248 is measured to determine whether the drop of body fluid has reached the capillary opening 244.

In another embodiment, the sensors 248 act as electrical contacts so that when a sufficient amount of fluid collects on the skin, the fluid contacts the sensors 248, thereby closing an electrical circuit between the sensors 248 and the skin. In another form, the detector 246 senses the fluid amount by detecting closure of a circuit between the sensors 248, which occurs when the fluid is about to fill the capillary channel opening 244. It is contemplated that detector 246 in other embodiments can use light or thermal imaging to detect fluid sufficiency. For instance, one the sensors 248 emits light and the other sensor detects the light. In one particular example, one of the sensors 248 is an LED that shines light towards the skin, and the other sensor 246 is a light detector, such as a photodiode or a CCD, that senses light reflected from the skin. Based on the sensed light, the sampling device is able to determine the amount or rate of body fluid bled from the incision. Again, these light based sensors can be used for location determination purposes, such as through a PSD. Alternatively or additionally, the sensors 248 sense the body fluid by shining the light between the sensors 248 so that the fluid is detected when the light beam across the capillary channel opening 244 is broken. It is contemplated that in still other embodiments the sensors 248 can use ultrasonic detection for both fluid sufficiency detection as well as range finding for the test strip 236. Nevertheless, it should be appreciated that combinations of the above-described techniques can be used as well as other techniques can be used to sense the body fluid.

Figure 9:
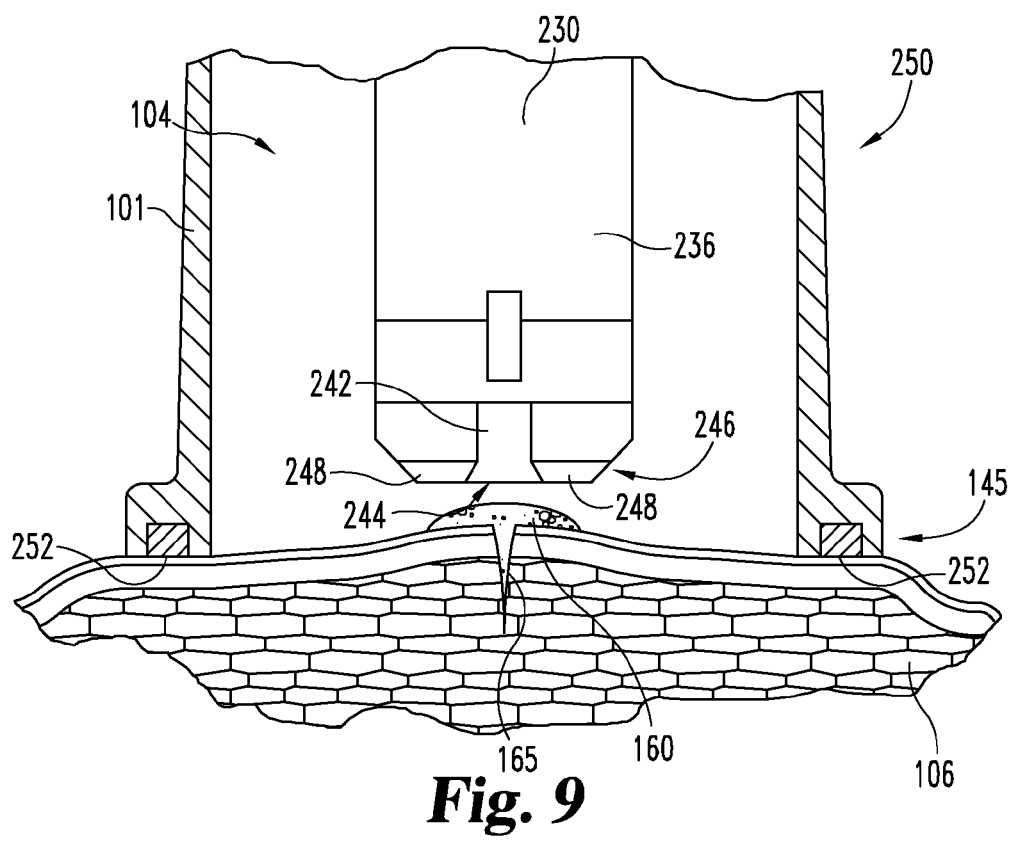
FIG. 9 is a partial cross-sectional view of the FIG. 6 device after creating an incision.

An enlarged partial cross sectional view of the integrated lancing test strip 230 during fluid detection is illustrated in FIG. 9. As shown, the integrated lancing test strip 230 is incorporated in a sampling device or meter 250. Like the FIG. 1 embodiment, the sampling device 250 in FIG. 9 includes firing mechanism 115 that is coupled to the connection portion 238 of the integrated lancing test strip 230. Via communication pathways 155, the firing mechanism 115 is operatively coupled to controller 150, and the controller 150 is operatively coupled to I/O device 157. This forms an operative connection between the integrated lancing test strip 230 and the controller 150 so that fluid detection information and test results, as well as other information, can be communicated between the integrated lancing test strip 230 and the controller 150. As depicted, the sampling device 250 includes housing 101 with collection chamber 104 in which the integrated lancing test strip 230 is disposed. Expression device 145 for expressing fluid is disposed around the opening of the collection chamber 104. In the illustrated embodiment, the expression device 145 includes one or more electrodes 252 that are operatively coupled to the controller 150 so as to utilize electrical stimulation to enhance bleeding and reduce pain associated with lancing. For examples of electrode configurations, please refer to U.S. patent application Ser. No. 10/791,173, filed Mar. 2, 2004, that is entitled "Method and Apparatus for Electrical Stimulation to Enhance Lancing Device Performance" which is hereby incorporated by reference in its entirety. Before lancing the skin 106, the electrodes 252 can electrically stimulate the skin at various frequencies and voltages to dilate the vessels in the skin 106 as well as deadened pain receptors in the skin 106. After the lancet needle 233 creates the incision 165, the electrodes 252 electrically stimulate the skin 106 to enhance fluid flow of the body fluid 160 from the incision 165. It should be recognized that other types of fluid expression techniques, such as vacuum and/or pressure based expression techniques, can be used along with electrical stimulation. Alternatively or additionally, the skin 106 can be re-lanced with a greater penetration depth, with a change in lancing angle and/or at a different location.

In conjunction with the detector 246 on the integrated lancing test strip 230, the electrodes 252 in one embodiment are used to determine the sufficiency of the body fluid 160 from the incision 165. Before the incision 165 is formed, the electrodes 252 apply a voltage to the skin 106 (via a direct and/or alternating current), and the sensors 248 on the integrated lancing test strip 230 measures the capacitance between the sensors 248 and the skin, either directly or indirectly. For instance, the sensors 248 in one form are used to measure the cut off frequency when the electrodes 252 apply an alternating current at a specified frequency to the skin 106 (i.e., acts like a band pass filter). In one form, the controller 150 uses the readings before lancing as a base line for determining body fluid sufficiency as well as for location determination purposes, if needed. To enhance accuracy, the user prior to use can load calibration test strips that have spacing members or portions at their ends with known dielectric properties and known spacing distances so that the controller 150 can be calibrated to the individual. The spacing portions on the ends of the calibration test strips create a specific distance and dielectric value between the skin 106 and the sensors 246 so that controller 150 is able to account for variations in skin properties. It is contemplated that in other embodiments the calibration test strips may not be needed. During lancing, the firing mechanism 115 extends the lancet needle 233 from the integrated lancing test strip 230 to form the incision 165, and subsequently, retracts the lancet needle 233. In one form, the electrodes 252 stimulate the skin 106 as the skin 106 is lanced, and in other forms, the electrodes 252 do not stimulate the skin 106 prior to or during lancing.

Once the incision 165 is created, the electrodes 252 apply to the skin 106 a specified electrical signal, such as having a specific voltage, current and/or frequency, and the detector 246 via the sensors 248 measure the capacitance between the sensors 248 and the skin 106. It should be appreciated that in further embodiments other electrical properties, like resistance, impedance and/or inductance, can be used to detect the amount of body fluid 160. As the body fluid 160 emerges from the incision, the dielectric properties of the body fluid 160 changes the capacitance level between the sensors 248 and the skin 106. The expression device 145 via the electrodes 252 or in some other manner, such as through a vacuum, continues to express body fluid 160 from the incision 165, until a specified change in capacitance level from the base line is achieved. At the specified level, the controller 150 considers the amount of fluid 160 on the skin 106 to be sufficient for fluid collection. In other forms, the controller 150 monitors the rate at which capacitance changes in order to determine flow rate of the body fluid 160. Once the designated change in capacitance is achieved, indicating that a sufficient amount of fluid is available for collection or flowing at a sufficient rate to eventually reach the desired sampling amount, the controller 150 ceases expression of the body fluid 160, if so desired, and initiates fluid collection.

To collect the body fluid 160, the controller 150 through the firing mechanism 115 moves the capillary channel opening 244 of the integrated lancing test strip 230 towards the skin 106. As the integrated lancing test strip 230 moves, the controller 150 in one embodiment monitors the capacitance readings from the sensors 248 to locate the position of the capillary channel opening 244. As mentioned before, if the channel opening 244 is positioned too far away from the drop of fluid 160, the integrated lancing test strip 230 will not be able to collect the body fluid 160, but if the integrated lancing test strip 230 is pressed too close or hard against the skin 106, fluid flow to the incision 165 can become constricted. When the sampling device 250 is pressed against the skin 106, the skin 106 can tend to bulge, which can change the distance between the channel opening 244 and the skin 106, and due to variations in elasticity in the skin 106, the bulging of the skin 106 can vary from body part to body part and/or from person to person. By performing proximity detection with the detector 246, the controller 150 is able to position the integrated lancing test strip 230 close enough to the skin 106 to collect the body fluid 160, but not too close so as to constrict fluid flow. As should be recognized, the proximity or range detection feature can also be used during lancing to control the penetration depth of the lancet 232 by compensating for bulging of the skin 106. Moreover, it is contemplated that the electrodes 252 can be optional in other embodiments. For example, to detect fluid sufficiency, a known voltage and/or an alternating current can just be applied to the sensors 248 in order to sense changes in capacitance, impedance or other electrical properties as body fluid 160 fills the space between the skin 106 and the detector 246. Again, it should be appreciated that the integrated lancing test strip 230 can sense fluid sufficiency in other manners as well.

Figure 10:
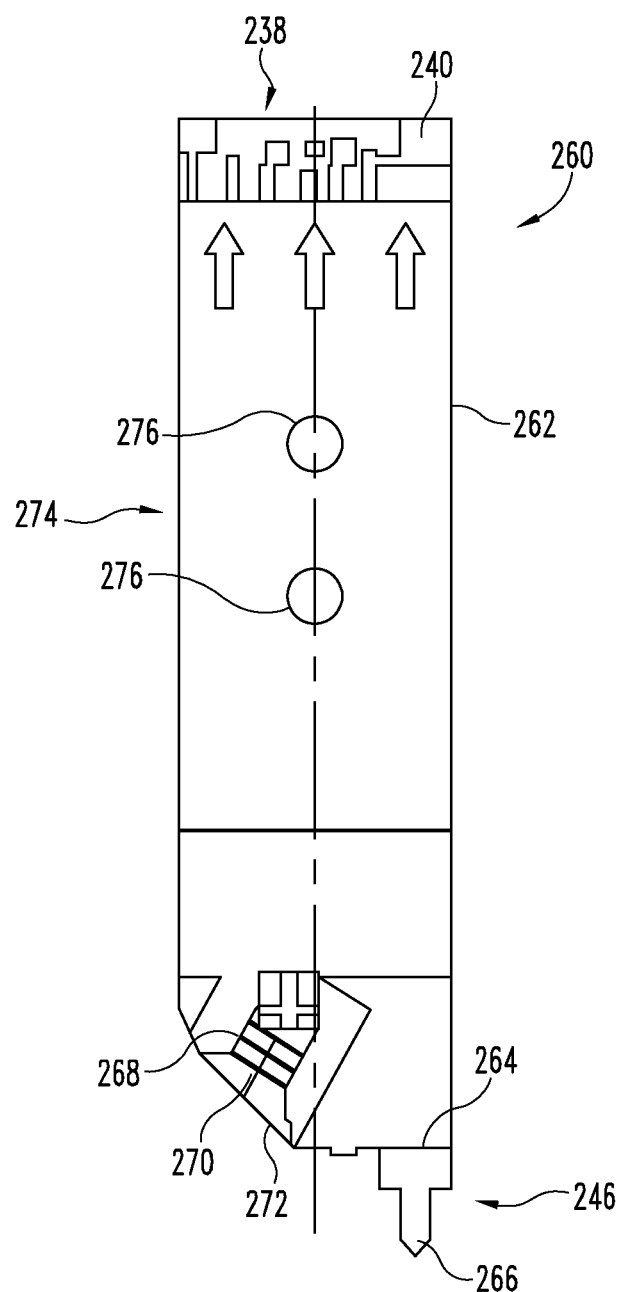
FIG. 10 is a top view of an integrated lancing test strip according to a further embodiment.

An example of an integrated lancing test strip 260 according to another embodiment is illustrated in FIG. 10. The FIG. 10 integrated lancing strip shares a number of features in common with the one described above as well as with the one described in U.S. patent application Ser. No. 11/103,871, filed Apr. 12, 2005, entitled "Integrated Lancing Test Strip With Retractable Lancet" which is hereby incorporated by reference in its entirety. For the sake of clarity as well as brevity, the common features will not be again described in great detail below.

As shown in FIG. 10, the integrated lancing test strip 260 includes a test strip 262 that has connector portion 238 with contacts 240 and a lancet 264 that is coupled the test strip 262. In the illustrated embodiment, the lancet 264 is fixed to the test strip 262. However, the lancet 264 in other embodiments is coupled to the test strip 262 in a moveable manner, such as in the FIG. 6 embodiment. In the FIG. 10 embodiment, the test strip 262 is an electrochemical type test strip, but it should be once more appreciated that other types of test strips can be used, such as a colorimetric type test strip. As can be seen, the lancet 264 is positioned offset from the central longitudinal axis of the integrated lancing test strip 260 such that the lancet 264 extends along one side of the test strip 262, parallel to the longitudinal axis. To provide a compact profile, the lancet 264 in the depicted embodiment is generally flat, and the lancet 264 includes a lancet tip 266 for forming an incision in tissue.

In the illustrated embodiment, the integrated lancing test strip 260 has fluid detector 246 for sensing the sufficiency of the body fluid on the tissue, and the fluid detector 246 in the depicted example includes the lancet 264. In the illustrated embodiment, the lancet 264 is made of a conductive material and is operatively coupled to one or more of the contacts 240 at the connection portion 238, which in turn are operatively coupled to the controller 150 via firing mechanism 115. The lancet 264 acts like an electrical contact so that when the body fluid reaches the lancet tip 266, an electrical circuit is formed such that the controller 150 is able to detect fluid sufficiency based on the closure of the circuit. In another embodiment, it is contemplated that the detector 246 for the integrated lancing test strip 260 of FIG. 10 can, additionally or alternatively, include the sensors 248 of the type described above with reference to FIG. 6.

Referring to FIG. 10, the test strip 262 defines a capillary channel 268 that has an analysis portion with electrodes and reagents for analyzing the fluid sample. The capillary channel 268 has an opening 270 that is offset from the longitudinal axis of the test strip 262 and slanted at an angle relative to the longitudinal axis. In one form, the angle between the capillary opening 270 and the longitudinal axis is an oblique angle. As shown, the capillary channel 268 has a boomerang shape, and the capillary channel opening 270 is Y-shaped with a curved opening. However, it is envisioned that the channel 268 can be shaped differently in other embodiments. The illustrated test strip 262 has a generally rectangular shape, with the exception that the test strip 262 has a truncated corner 272 at the capillary channel opening 270. The truncated corner 272 allows the capillary channel opening 270 to be rotated over the incision site without having the test strip 262 contacting the skin or the body fluid drop, which could potentially smear the drop of fluid.

By having the ability to rotate the lancet 264 out of the way, the capillary channel 268 is able to collect the fluid sample without the lancet 264 interfering with the sample collection. In some embodiments, the integrated lancing test strip 260 is rotated between 30° to 180° to collect the fluid sample. To minimize the rotation of the test strip 262, the lancet 264 and the capillary channel 268 are located near the same end of the test strip 262. It is nonetheless contemplated that the lancet 264 and the capillary channel 268 can be positioned differently for other embodiments. For example, the orientation of the lancet 264 and the capillary channel 268 can be reversed such that the capillary channel 268 extends parallel to the longitudinal axis and the lancet 264 extends in a nonparallel manner relative to the longitudinal axis. The integrated lancing test strip 260 in one form is rotated manually by the user after the incision is formed, and in another form, the meter automatically rotates the integrated lancing test strip 260. To automatically rotate the integrated lancing test strip 260, the integrated lancing test strip 260 includes a coupling structure 274 that allows the firing mechanism 115, actuator 135, or some other type of device, to rotate the integrated lancing test strip 260. In the illustrated embodiment, the test strip 262 has one or more engagement holes 276 through which the test strip 262 is held and rotated. It is envisioned that other types of coupling structures with different configurations can be used to rotate the integrated lancing test strip 260.

Figure 13:
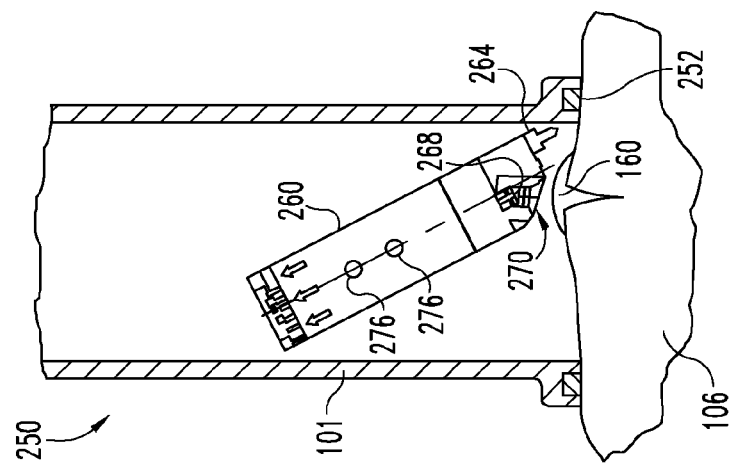
FIG. 13 shows the FIG. 10 device positioned to sample body fluid from the incision.
Figure 12:
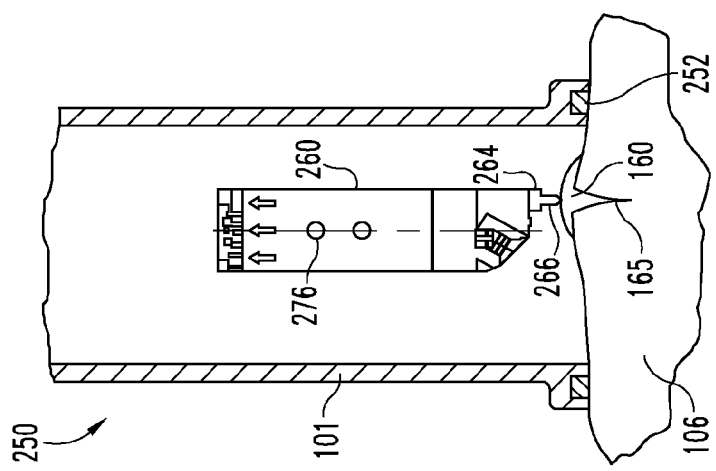
FIG. 12 shows the FIG. 10 device as the lancet is retracted from the incision.
Figure 11:
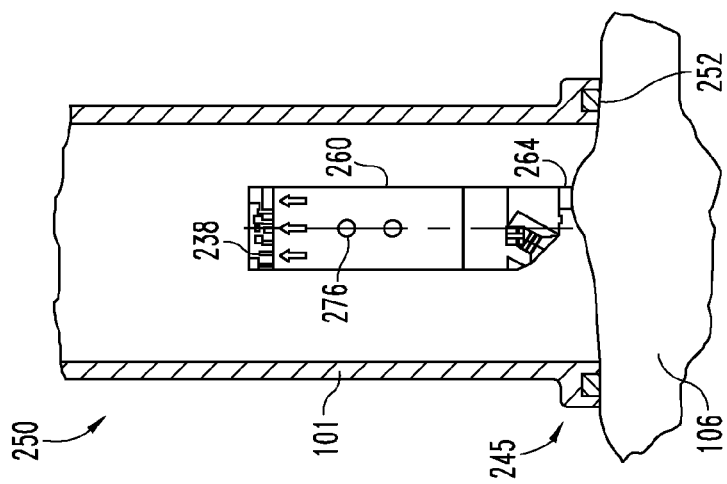
FIG. 11 shows the FIG. 10 device lancing the skin to form an incision.

Referring now to FIGS. 11, 12 and 13, there is illustrated the various stages for collecting and analyzing a body fluid sample with the integrated lancing test strip 260. With reference to FIG. 11, the integrated lancing test strip 260 is loaded into sampling device or meter 250 that is similar to the ones shown in FIGS. 1 and 9 with the connection portion 238 coupled to the firing mechanism 115. Like before, the expression member 245 includes one or more electrodes 252 that are operatively coupled to the controller 150, but it again should be appreciated that fluid can be expressed using other types of expression devices. In one embodiment, the electrodes 252, the skin 106, body fluid 160 and the lancet 264 are used to form a circuit with the controller 150 for sensing fluid sufficiency via resistance or other electrical property. In another embodiment, the electrodes 252 are optional such that fluid sufficiency is detected when the lancet 264 is grounded upon contacting the body fluid 160. If so desired, the expression member 245 can stimulate the skin prior to and/or during lancing to stimulate fluid flow or deaden pain. As shown in FIG. 11, the lancet 264 lances the skin 106 by having the entire integrated lancing test strip 260 fired towards the skin 106 by the firing mechanism 115. During lancing, the controller 150 can sense for misfiring of the integrated lancing test strip 230 by determining if a circuit was formed between the lancet 264 and the skin 106. If the circuit does not close while lancing, the controller 150 can re-fire the lancet 264 or take other appropriate actions to correct the problem.

After the incision 165 is created, the controller 150 via the firing mechanism 115 retracts the lancet 264 a specified distance from the surface of the skin or tissue 106. To promote fluid flow from the incision 165, as is illustrated in FIG. 12, the controller 150 in one form activates the expression device 245 prior to, during and/or subsequent to lancing to enhance flow of the body fluid 160 from the incision 165. The controller 150 continues the expression of fluid until the body fluid 160 contacts the lancet tip 266, which is an indication that a sufficient sample size has collected on the skin 106. In another form, the controller 150 delays initiation of expression for a specified time so as to give the body fluid 160 the ability to naturally emerge from the incision 165. After the specified time period elapses, if the body fluid 160 does not contact the lancet 264, then the controller activates the expression device 245 to express additional fluid 160 until contact between the lancet 264 and the fluid 160 is established. Once a sufficient amount of fluid 160 collects on the skin 106, the entire integrated lancing test strip 260 is rotated so that the capillary channel 268 is able to collect body fluid 160 from the incision 165, as is depicted in FIG. 13. The test strip 262 is rotated such the lancet 264 moves away giving a clear path for the capillary 268 of the test strip 262 to contact the body fluid 160. In the embodiment where the lancet 264 is not fixed to the test strip 262, the lancet 264 can be retracted inside the integrated lancing test strip 260 so as to further reduce the chance of the lancet 264 interfering with fluid collection and the risk of accidentally stabbing oneself with the lancet 264. The integrated lancing test strip 260 can be rotated manually by the user, for example by repositioning the entire meter 250, or the entire integrated lancing test strip 260 can be rotated automatically by the firing mechanism 115.

Upon rotation, the firing mechanism 115 moves the capillary channel opening 270 towards the body fluid 160, and the body fluid 160 is then drawn by the capillary channel 268 into the analysis area where the sample is analyzed. In another embodiment, the integrated lancing test strip 260, alternatively or additionally, includes one or more of the previously described sensors 248 positioned at the capillary channel opening 270 in order to sense fluid sufficiency and/or locate the capillary channel opening 270. For example, the integrated lancing test strip 260 in one form employs a two-step sensing technique in which the lancet 264 senses initial fluid sufficiency and the sensors 248 double check the fluid sufficiency reading. If the sensors 248 sense that the fluid amount or flow rate is insufficient for testing, the controller 150 can activate the expression device 245 so as to express more body fluid 160. Fluid 160 can also be expressed in the manner as was described with reference to FIG. 5. When an insufficient amount of the body fluid 160 is present, I/O device 157 can also indicate fluid insufficiency to prevent premature removal of the meter 250. In the illustrated embodiment, the integrated lancing test strip 260 is connected to the meter 250 through the strip connector 238, and the results from the analysis are transferred to the meter 250 through the connector 238. Results from the analysis are presented with the I/O device 157 and/or transferred to a computer for further analysis.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. An apparatus, comprising:
    a test strip including
        a capillary channel having an opening for drawing body fluid from tissue,
        an analysis portion for analyzing the body fluid, and
        a fluid detector disposed at the opening of the capillary channel;
    one or more electrodes configured to contact the tissue; and
    the fluid detector being configured to measure a cutoff frequency when the one or more electrodes apply an alternating current to the tissue.

2. The apparatus of claim 1, wherein the fluid detector is configured to sense sufficiency of the body fluid on the tissue before the body fluid is drawn into the capillary channel.

3. The apparatus of claim 2, wherein the fluid detector is configured to sense an amount of the body fluid on the tissue.

4. The apparatus of claim 2, wherein the fluid detector is configured to sense the rate of emergence of the body fluid from an incision in the tissue.

5. The apparatus of claim 1, wherein the fluid detector is configured to sense distance between the opening of the capillary channel and the tissue.

6. The apparatus of claim 1, wherein the fluid detector is configured to measure capacitance between the fluid detector and the tissue.

7. The apparatus of claim 1, wherein the fluid detector is configured to sense the body fluid when the body fluid contacts the fluid detector to create a closed circuit between the fluid detector and the tissue.

8. The apparatus of claim 1, further comprising:
    a lancet coupled to the test strip for creating an incision in the tissue.

9. The apparatus of claim 8, further comprising:
    a controller configured to sense misfiring of the lancet by determining if a closed circuit was formed between the lancet and the tissue during lancing.

10. The apparatus of claim 8, further comprising:
    a controller configured to sense sufficiency of the body fluid when the body fluid contacts the lancet to form a circuit with the controller.

11. The apparatus of claim 8, wherein:
    the lancet is fixed to the test strip; and
    the capillary channel has an opening that is positioned at an oblique angle relative to the lancet.

12. The apparatus of claim 8, wherein the lancet is coupled to the test strip in a slidable manner to allow extension of the lancet from the test strip.

13. The apparatus of claim 1, wherein the test strip includes an optical test strip.

14. The apparatus of claim 1, wherein the test strip includes an electrochemical test strip.

15. An apparatus, comprising:
- a test strip including
  - a capillary channel having an opening for drawing body fluid from tissue,
  - an analysis portion for analyzing the body fluid, and
  - a fluid detector disposed at the opening of the capillary channel, wherein the fluid detector is integrated into one end of the test strip, and wherein the fluid detector is exposed at the end of the test strip; and
- wherein the fluid detector is an imaging sensor.

16. The apparatus of claim 15, wherein the fluid detector is a light imaging sensor.

17. The apparatus of claim 15, wherein the fluid detector is a thermal imaging sensor.

18. The apparatus of claim 15, wherein the fluid detector includes a light emitting diode configured to shine light onto the tissue and a photodiode configured to sense the light reflected from the tissue.

19. The apparatus of claim 15 further comprising:
- the fluid detector having parts at opposite sides of the opening of the capillary channel; and
- the fluid detector being configured to shine light across the opening of the capillary channel to sense the body fluid.

20. An apparatus, comprising:
- a test strip including
  - a capillary channel having an opening for drawing body fluid from tissue,
  - an analysis portion for analyzing the body fluid, and
  - a fluid detector disposed at the opening of the capillary channel, wherein
- the fluid detector is disposed at one end of the test strip, and wherein the fluid
- detector is exposed at the end of the test strip;
- one or more electrodes configured to contact the tissue; and
- wherein the fluid detector is configured to measure capacitance between the fluid detector and the tissue via the one or more electrodes.

* * * * *